US008652453B2

(12) United States Patent
Nakamura et al.

(10) Patent No.: US 8,652,453 B2
(45) Date of Patent: Feb. 18, 2014

(54) HAIR COSMETIC

(75) Inventors: Keiko Nakamura, Yokohama (JP); Taizo Fujiyama, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/576,884

(22) PCT Filed: Nov. 16, 2010

(86) PCT No.: PCT/JP2010/070342
§ 371 (c)(1),
(2), (4) Date: Aug. 2, 2012

(87) PCT Pub. No.: WO2011/114577
PCT Pub. Date: Sep. 22, 2011

(65) Prior Publication Data
US 2012/0328551 A1 Dec. 27, 2012

(30) Foreign Application Priority Data

Mar. 17, 2010 (JP) .................................. 2010-061308

(51) Int. Cl.
*A61K 8/34* (2006.01)
*A61K 8/37* (2006.01)
*A61K 8/92* (2006.01)
*A61Q 5/12* (2006.01)

(52) U.S. Cl.
USPC ................ 424/70.11; 424/70.12; 424/70.122

(58) Field of Classification Search
USPC ................ 424/70.11, 70.12, 70.122
See application file for complete search history.

(56) References Cited

FOREIGN PATENT DOCUMENTS

| JP | 55-136214 | | 10/1980 |
| JP | 63-243019 | | 10/1988 |
| JP | 01-272513 | | 10/1989 |
| JP | 08-040839 | | 2/1996 |
| JP | 2005-206552 | | 8/2005 |
| JP | 2007-051078 | | 3/2007 |
| JP | 2008-137916 | * | 6/2008 |
| JP | 2009-221143 | * | 10/2009 |
| JP | 2011-195471 A | | 10/2011 |
| WO | WO 2011/114577 A1 | | 9/2011 |

OTHER PUBLICATIONS

PCT/JP2010/070342, International Search Report mailed Feb. 22, 2011, 3 pages—Japanese, 2 pages—Full English Translation.
JPO Decision of Refusal, Oct. 27, 2011, Japanese and full English translation.
JPO Decision of Refusal, Feb, 17, 2011, Japanese and full English translation.
JPO Decsion to Grant, Mar. 12, 2012, Japanese and full English translation.
JPO allowed claims, Japanese and full English translation.
PCT/JP2010/070342, International Preliminary Report issued Oct. 23, 2012, 2 pages—English Translation.
PCT/JP2010/070342, Written Opinion mailed Feb. 22, 2011, 6 pages—English.

\* cited by examiner

*Primary Examiner* — Richard Schnizer
*Assistant Examiner* — Alma Pipic
(74) *Attorney, Agent, or Firm* — Andrew F. Young, Esq.; Lackenbach Siegel, LLP

(57) ABSTRACT

A new hair cosmetic composition containing (a) a 40-90 wt % volatile oil component, (b) 0.1-20 wt % a combination of polyoxyethylene, polyoxypropylene, butylene, dimethylpolysiloxane copolymers, and (c) 0.1-30 wt % ethanol. This hair cosmetic composition may be mainly used in a hair oil for superior sensation during use and superior stability over time.

3 Claims, No Drawings

HAIR COSMETIC

CROSS REFERENCE TO RELATED APPLICATIONS

This application claims priority to International Ser. No. PCT/JP2010/070342 filed Nov. 16, 2010, the entire contents of which are incorporated herein fully by reference, which in turn claims priority to JP Serial No. JP 2010-061308 filed on Mar. 17, 2010.

TECHNICAL FIELD

The present invention relates to a hair cosmetic. More specifically, it relates to a hair cosmetic mainly used as hair oil that exhibits a superior sensation during use and superior stability over time.

BACKGROUND ART

Hair oil is a hair cosmetic that is used to supplement oil components in the hair and give it gloss, smoothness, and flexibility. As for the constituent ingredients, the main ingredient is plant oils (Camellia seed oil, olive oil, etc.) and/or mineral oil (liquid paraffin) having a low viscosity, to which higher fatty acid esters, squalane, silicone oils, etc. are added (Non-Patent Document 1).

For example, Patent Document 1 discloses a hair cosmetic containing a highly polymerized silicone that is superior in spreadability, smoothness, and tactile softness at the time of application on the hair and, after application on the hair, gives a smooth tactile sensation, softness, and appropriate sense of togetherness. Said hair cosmetic contains, as the constituent ingredients, a specific highly polymerized silicone, a volatile hydrocarbon oil, a cholesterol derivative, and a low-viscosity silicone oil. A non-water system is preferable, but, depending on the configuration and/or formulation form, a small amount of water and/or lower alcohol (ethanol) may be contained. However, the hair cosmetic described in Patent Document 1 does not contain the (b) ingredient of the present invention as a constituent ingredient and therefore the sensation during use is not necessarily as good as that of the invention of the present application.

Patent Document 2 is an invention by the applicant of the present application and it discloses hair cosmetics such as hair oil that give superior gloss and a smooth tactile sensation to the hair and also achieves opposing sensations during use, i.e. moist and loose tactile sensations. This hair cosmetic characteristically contains as constituent ingredients (A) 1-15 wt % of plant oils, (B) a volatile oil component, (C) a high molecular weight dimethylpolysiloxane, and (D) a dimethylpolysiloxane containing hydroxyl groups, polyoxyethylene groups and/or polyoxypropylene groups.

However, the hair oil described in Patent Document 2 does not contain ethanol, which is an essential ingredient in the invention of the present application, and therefore its sensation during use is worse than the invention of the present application. Furthermore, when the (b) ingredient of the invention of the present application is added to the invention described in Patent Document 2, the stability over time may deteriorate.

PRIOR ART DOCUMENTS

Patent Documents

Patent Document 1: JP 2007-223930 A
Patent Document 2: JP 2009-221143 A

Non-Patent Documents

Non-Patent Document 1: "Shin-Keshohin-Gaku [New Cosmetic Science] (Nanzando)", (First edition, third print) Aug. 20, 1997, pp. 438-439, Editor: Takeo Mitsui

DISCLOSURE OF INVENTION

Technical Problem

In view of the aforementioned problem, the inventors conducted earnest research to manufacture a new hair oil with a superior sensation during use and stability and discovered that adding both a dimethylpolysiloxane of a specific structure and ethanol to a specific hair oil composition can surprisingly provide a hair oil that is absorbed well in the hair, exhibits a high level of ease of combing, hair togetherness, and hair slipperiness, solves the problem of hair oil generally being oily when applied, solves the unique problem of hair oil that the hair becomes dry over time, and improves the hair oil composition's stability over time, and thus completed the present invention.

The object of the present invention is to provide a new hair oil that exhibits a superior sensation during use and stability over time.

Technical Solution

That is, the present invention provides a hair cosmetic comprising the following ingredients (a) through (c):

(a) A Volatile oil component: 40-95 wt %
(b) A Highly polymerized straight chain block-type polyoxyethylene/polyoxypropylene/butylene/dimethylpolysiloxane copolymer: 0.1-20 wt %
(c) Ethanol: 0.1-30 wt %

Also, the present invention provides the aforementioned hair cosmetic wherein said ingredient (b) is a dimethicone PEG block polymer having the following formula (1):

[Chemical formula 1]

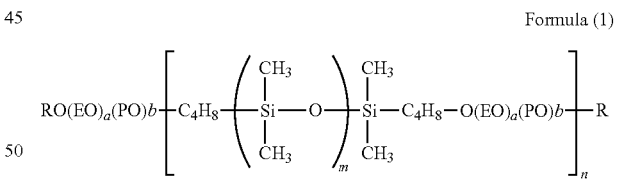

Formula (1)

(R denotes a straight chain or branched chain alkyl group, a and b denote integers 0-50, m denotes an integer 5-300. and n denotes an integer 1-40. EO represents oxyethylene group, and PO represents oxypropylene group.)

Furthermore, the present invention provides the aforementioned hair cosmetic that additionally comprises (d) one, two or more silicone gums selected from a group consisting of high molecular weight polysiloxane, highly polymerized dimethiconol, amino-modified high molecular weight silicone, and ammonium-modified high molecular weight silicone.

Also, the present invention provides the aforementioned hair cosmetic that additionally comprises (e) plant oils and/or polar oils containing one or more ester bonds.

Furthermore, the present invention provides the aforementioned hair cosmetic wherein said hair cosmetic is a non-water system hair oil which substantially does not contain water.

Advantageous Effects (1) The hair cosmetic (hair oil) of the present invention uses ethanol, which is more volatile than volatile oil components, and therefore the solvent evaporates faster and absorption occurs faster whether the hair is wet or dry, thereby greatly improving the oiliness right after application, which has been a shortcoming of hair oils.
(2) The hair cosmetic (hair oil) of the present invention improves a shortcoming of hair oil in that the hair becomes dry over time even though it is moist right after the application. That is, in a case where the solvent of the hair cosmetic is only a volatile oil component and a dryer is not used after application, sometimes there is a problem in that the hair is moist right after application but becomes dry over time. The moistness right after the application is due not only to the oil component remaining in the hair but also to the sensation during use from the volatile oil component that has not completely evaporated. However, the use of ethanol accelerates the evaporation of the volatile oil component from the hair so it is less likely to remain, and as a result the sensation during use right after application is mostly from the residual oil components (residual oil components other than the volatile oil component and ethanol); therefore the sensation during use doesn't change over time and the problem of dryness as mentioned above is improved.
(3) When the only solvent used in the present invention is a volatile oil component, the highly hydrophilic portion of the (b) ingredient sometimes precipitates over time, but the concurrent use of ethanol prevents the precipitation and provides superior stability over time.
(4) The present invention significantly improves the sensation during use such as absorption in the hair and the sensation of running fingers through the hair by blending in ingredient (b), the dimethicone PEG block polymer.

BEST MODE FOR CARRYING OUT THE INVENTION (a) A Volatile Oil Component: 40-95 wt %

The present invention is a hair cosmetic intended for a hair oil and its main ingredient is a volatile oil component.
Examples of the volatile oil component used in the present invention include relatively low molecular weight hydrocarbon oils, relatively low molecular weight straight chain silicones, and relatively low molecular weight cyclic silicones; particularly preferable are light liquid isoparaffin, isododecane, isohexadecane, volatile dimethylpolysiloxanes, and cyclic polysiloxanes. Concrete examples include octamethylcyclotetrasiloxane, decamethylcyclopentasiloxane, dodecamethylcyclohexasiloxane, and hexadecamethylcycloheptasiloxane. Particularly preferable are light liquid isoparaffin, isodecane, and isohexadecane.
<Blend Ratio>
In the present invention, the blend ratio of the volatile oil component is preferably 40-95 wt %, more preferably 50-90 wt %, most preferably 60-85 wt % relative to the total amount of the hair cosmetic. By blending in a large amount of the volatile ingredient, the spreadability is improved and therefore uniform application on the hair becomes possible, resulting in a superior hair oil.

However, the present invention improves a shortcoming of hair oil in that the hair becomes dry over time even though it is moist right after the application. That is, in a case where the solvent of the hair cosmetic only contains a large amount of a volatile oil component as mentioned above and a dryer is not used after application, sometimes there is a problem in that the hair is moist right after application but becomes dry over time. The moistness right after the application is due not only to the oil component remaining in the hair but also to the sensation during use from the volatile oil component that has not completely evaporated. However, the use of ethanol accelerates the evaporation of the volatile oil component from the hair so it is less likely to remain, and as a result the sensation during use right after application is mostly from the residual oil components (residual oil components other than the volatile oil component and ethanol) therefore the sensation during use doesn't change over time and the aforementioned problem of dryness as mentioned above is improved.
<(b) A Highly Polymerized Straight Chain Block-Type Polyoxyethylene/Polyoxypropylene/Butylene/Dimethylpolysiloxane Copolymer: 0.1-20 wt %>
The highly polymerized straight chain block-type polyoxyethylene/polyoxypropylene/butylene/dimethylpolysiloxane copolymer used in the present invention stands for a polyether-modified silicone that results from block copolymerization of polyoxyalkylene groups in a straight chain fashion. The block copolymerized polyether-modified silicone represented by the following formula 1 is preferable. In the present invention, the role of said copolymer for the hair cosmetic is to maintain a good sensation during use in terms of absorption into the hair and ease of running fingers through the hair.

[Chemical formula 2]

Formula (1)

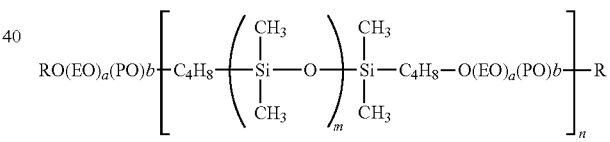

(R denotes a straight chain or branched chain alkyl group, a and b denote integers 0-50 (a+b may not be 0), m denotes an integer 5-300, and n denotes an integer 1-40. EO represents oxyethylene group, and PO represents oxypropylene group.)
For a, b, m, and n in the formula, preferable ranges are 5-10 for a, 5-10 for b, 200-300 for m, and 30-40 for n.
The polyether-modified silicone in formula 1 can be modified in various ways; specifically, in the aforementioned formula 1, some methyl groups can be replaced with phenyl groups and butylene groups can be replaced with other alkylene groups such as ethylene groups. Also, some oxyethylene groups and propylene groups may be replaced with other oxyalkylene groups such as oxybutylene. In the present application, sometimes the modified product of formula (1) is regarded as the equivalent of the block copolymerized polyether-modified silicone of formula (1) and this equivalent is included in what we call "a dimethicone PEG block polymer."
The polyether-modified silicone of formula (1), in terms of chemical compound designation, is called a polyoxyethylene/polyoxypropylene/butylene/dimethylpolysiloxane copolymer, polyoxyethylene/butylene/dimethylpolysiloxane copolymer, polysilicone-13, etc.

In the present invention, commercially available products can be used. Examples of preferable commercial products include block copolymerized poly(oxyethylene/oxypropylene)/alkylene/methylpolysiloxane copolymer, FZ-2250, and FZ-2233 (Dow Corning Toray Company Ltd.).

<Blend Ratio>

The blend ratio of the polyoxyethylene/polyoxypropylene/butylene/dimethylpolysiloxane copolymer is preferably 0.1-20 wt %, more preferably 0.5-10 wt %, most preferably 1-2 wt % relative to the total amount of the hair cosmetic. If the blend ratio is too low, then the effect of improving absorption into the hair and ease of running fingers through the hair is not manifested; if it is too high, then stickiness arises.

The commercial product FZ-2250 (Dow Corning Toray Company Ltd.) is a mixture of 35 wt % of the original substance and 65 wt % of isoparaffin, and therefore the aforementioned blend ratio is required to be the actual net blend ratio of the original substance.

<(c) Ethanol: 0.1-30 wt %>

The most significant characteristic of the present invention is to blend in a prescribed amount of ethanol, as a lower alcohol, in combination with the aforementioned essential ingredients (a) and (b).

That is, the present invention uses ethanol, which is more volatile than ingredient (a) a volatile oil component, and therefore the solvent evaporates faster and absorption occurs faster whether the hair is wet or dry, thereby greatly improving the oiliness right after application, which has been a shortcoming of hair oils.

Also, this improves the shortcoming of hair oil in that the hair becomes dry over time even though it is moist right after the application. That is, in a case where the solvent of the hair cosmetic is only a volatile oil component and a dryer is not used after application, sometimes there is a problem in that the hair is moist right after application but becomes dry over time. The moistness right after the application is due not only to the oil component remaining in the hair but also to the sensation during use from the volatile oil component that has not completely evaporated. However, the use of ethanol accelerates the evaporation of the volatile oil component from the hair so it is less likely to remain, and as a result the sensation during use right after application is mostly from the residual oil components (residual oil components other than the volatile oil component and ethanol); therefore the sensation during use doesn't change over time and the problem of dryness as mentioned above is improved.

When the only solvent used in the present invention is the volatile oil component, the highly hydrophilic portion of "a dimethicone PEG block polymer" of the (b) ingredient sometimes precipitates over time. But the concurrent use of ethanol prevent the precipitation and provides superior stability over time.

<Blend Ratio>

The blend ratio of ethanol is preferably 0.1-30 wt %, more preferably 0.5-20 wt %, most preferably 1-15 wt % relative to the total amount of the hair cosmetic. If the blend ratio is too low, then the aforementioned effects are not manifested sufficiently; and, if it is too high, then the low temperature stability becomes poor.

<(d) One, Two or More Silicone Gums Selected from a Group Consisting of High Molecular Weight Polysiloxanes, Highly Polymerized Dimethiconols, Amino-Modified High Molecular Weight Silicones, and Ammonium-Modified High Molecular Weight Silicones>

It is preferable to also add a specific silicone gum to the present invention. For the silicone gum to be used in the present invention, high molecular weight polysiloxanes, highly polymerized dimethiconols, amino-modified high molecular weight silicones, and ammonium-modified high molecular weight silicones are preferable; they manifest superior effects in terms of the split-end repair effect, silkiness, and smoothness.

The high molecular weight polysiloxane is a high molecular weight polysiloxane represented by the following general formula, n is preferably 5,000-8,000.

[Chemical formula 3]

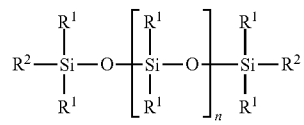

[In this formula, $R^1$s denote, identical or different, either methyl groups or phenyl groups (all may not be phenyl groups), and $R^2$s denote, identical or different, either methyl groups or hydroxyl groups, n denotes an integer 3,000-20,000.

The highly polymerized dimethiconol means the silicone gum represented by the following general formula.

[Chemical formula 4]

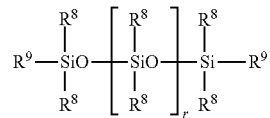

[In this formula, $R^8$s are independent of each other and either methyl groups or phenyl groups; under no circumstances are all the $R^8$s phenyl groups. $R^9$s denotes a hydroxyl group, r denotes the degree of polymerization; it is 3,000-20,000, preferably 5,000-8,000.]

Representative commercial products of highly polymerized dimethiconols include XF49-C2070 having a degree of polymerization of approximately 7,000 as well as X65-C2070 having a degree of polymerization of approximately 7,000 (from GE Toshiba Silicones Co. Ltd.).

The amino-modified high molecular weight silicone or ammonium-modified high molecular weight silicone stands for the amino-modified or ammonium-modified high molecular weight silicone represented by the following general formula.

[Chemical formula 5]

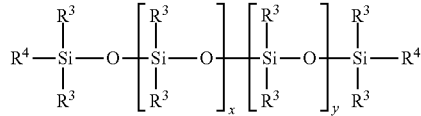

[In this formula, $R^3$s denote, identical or different, either methyl groups or phenyl groups (all may not be phenyl groups), and $R^4$s denote, identical or different, either methyl groups or hydroxyl groups. $R^5$ denotes a substituent having an amino group or an ammonium group represented by formula $R^6Z$ where $R^6$ denotes an alkylene group having 3 to 6 carbon atoms, Z denotes a monovalent group chosen from a group consisting of —N($R^7$)$_2$, —$N^+$($R^7$)$_3$$A^-$, —N($R^7$)(CH$_2$)$_a$N($R^7$)$_2$, —N($R^7$)(CH$_2$)$_4$$N^+$($R^7$)$_3$$A^-$ and —N($R^7$)(CH$_2$)$_n$N($R^7$)CO($R^8$) where $R^7$ denotes hydrogen or an alkyl group having a hydrogen or 1-4 carbon atoms, $R^8$ denotes an alkyl group having 1-4 carbon atoms, A denotes a Chlorine, Bromine, or Iodine atom and a denotes an integer 2-6, x and y each denotes a positive integer, x+y denotes an integer 3,000-20,000, and y/x is 1/500-1/10,000.]

<Blend Ratio>

The blend ratio of the aforementioned silicone gum is preferably 0.1-20 wt %, more preferably 0.3-20 wt %, most preferably 0.5-15 wt % relative to the total amount of the hair cosmetic.

<(e) A Plant Oil and/or Polar Oil Containing One or More Ester Bonds>

The present invention may additionally contain a plant oil and/or polar oil containing one or more ester bonds. The reason is to add moistness to the present invention.

Selection of the plant oil is not limited in particular; what can be used includes avocado oil, camellia seed oil, macadamia nut oil, corn oil, olive oil, rapeseed oil, sesame oil, apricot kernel oil, wheat germ oil, camellia kissi seed oil, castor oil, linseed oil, safflower oil, cotton seed oil, perilla oil, soybean oil, peanut oil, tea seed oil, Oleum Camelliae, Japanese nutmeg oil, rice bran oil, Chinese gimlet oil, Japan gimlet oil, jojoba oil, and germ oil.

Examples of usable polar oils having one or more ester bonds include esters such as cetyl-2-ethylhexanoate, 2-ethylhexyl palmitate, 2-octyldodecyl myristate, neopentyl glycol-2-ethylhexanoate, isopropyl myristate, myristyl myristate, pentaerythrityl tetra 2-ethylhexanote, di 2-ethylhexyl succinate, triethylhexanoin, and diisostearyl malate.

<Blend Ratio>

The blend ratio of the plant oil and/or polar oil containing one or more ester bonds is preferably 0.1-20 wt %, more preferably 0.5-20 wt %, most preferably 1-15 wt % relative to the total amount of the hair cosmetic.

<Non-Water System Hair Oil>

The hair cosmetic of the present invention, as a product, is preferably a non-water system hair oil; depending on the configuration and/or formulation form, it may contain a small amount of water and/or lower alcohol.

The present invention is also preferable when it is prepared as a hair oil composed only of (a)-(c).

Also, it is also preferable to add (d) a specific silicone gum, (e) a plant oil and/or polar oil containing one or more ester bond, or a methylpolysiloxane (dimethicone).

The hair cosmetic of the present invention can be prepared using a common method in accordance with the target formulation form by suitably blending in, in addition to the aforementioned essential ingredients, other components that are normally used in cosmetics, such as powder components, liquid fats and oils, solid fats and oils, waxes, hydrocarbons, higher fatty acids, higher alcohols, ester oils, silicone oils, anionic surfactants, cationic surfactants, amphoteric surfactants, nonionic surfactants, humectants, water-soluble polymers, thickeners, coating agents, ultraviolet light absorbents, sequestering agents, lower alcohols, polyhydric alcohols, sugars, amino acids, organic amines, polymer emulsions, pH adjusting agents, skin nutrients, vitamins, antioxidants, antioxidation assistants, and perfumes. The most preferable hair cosmetic in the present invention is a non-water system hair oil.

EXAMPLES

The invention is further described in specific detail through Examples. The present invention is not limited to these Examples. The blend ratios in Examples are in wt % (mass-percentage) units unless specified otherwise.

Examples 1-3 and Comparative Examples 1-5

Hair oils having the compositions described in the following Table 1 were prepared with a conventional method and the effects of the present invention were evaluated.

The evaluation of the effects was conducted by shampooing and towel-drying bundles of 100 hairs cut at the length of 20 cm, applying each hair oil on said bundles, followed by tactile sensing and visual observation.

The selected evaluation items in terms of the sensation during use were the absorption into the hair, absence of oiliness, and durable finish; sensory evaluation was conducted on each item based on the following criteria. The stability over time was also evaluated.

"Absorption into the Hair"
◎: Very good absorption
○: Good absorption
Δ: Not so good absorption
x: Poor absorption "Absence of Oiliness"
◎: Not oily at all
○: Not oily
Δ: Something oily
x: Oily "Durable Finish"
◎: Very durable
○: Durable
Δ: Not very durable
x: Not durable "Stability over time"
○: After one year of being left alone at room temperature, no separation or precipitation was visually observed.
x: After one year of being left alone at room temperature, separation or precipitation was visually observed.

TABLE 1

| | | | Comparative example 1 | Comparative example 2 | Example 1 | Comparative example 3 | Example 2 | Example 3 | Comparative example 4 | Comparative example 5 |
|---|---|---|---|---|---|---|---|---|---|---|
| Composition | (a) | Light liquid paraffin | Balance | Balance | Balance | Balance | Balance | Balance | Balance | Balance |
| | (b) | Dimethicone PEG block polymer *1 | 5 | — | 5 | 0.01 | 0.5 | 20 | 0.01 | 30 |
| | (c) | Ethanol | — | 5 | 5 | 0.01 | 0.1 | 30 | 40 | 0.01 |
| | | Dimethicone (5 cs) | 10 | 10 | 10 | 10 | 10 | 10 | 10 | 10 |
| Effects | | Absorption into the hair | ○ | Δ | ○ | X | ○ | ◎ | Δ | Δ |

TABLE 1-continued

|  | Comparative example 1 | Comparative example 2 | Example 1 | Comparative example 3 | Example 2 | Example 3 | Comparative example 4 | Comparative example 5 |
|---|---|---|---|---|---|---|---|---|
| Absence of oiliness | ○ | Δ | ○ | Δ | ○ | ◎ | ◎ | X |
| Durable finish | Δ | ○ | ○ | X | ○ | ◎ | ○ | Δ |
| Stability over time | X | ○ | ○ | ○ | ○ | ○ | X | X |

*1: FZ-2250 (from Dow Corning Toray Company Ltd.)

Other hair oils of the present invention are shown below. All these hair oils exhibit superior sensation during use and stability over time.

Example 4

Hair Oil

The following ingredients (1)-(9) were stirred, dissolved and mixed to obtain a liquid hair oil.

| Ingredient | wt % |
|---|---|
| (1) (a) Light liquid paraffin (IP Solvent 2028MU from Idemitsu Kosan Co., Ltd.) | Balance |
| (2) (b) Dimethicone PEG block polymer (FZ-2250 from Dow Corning Toray Company Ltd.) | 10.0 |
| (3) (c) Ethanol | 20.0 |
| (4) (d) High molecular weight polysiloxane (KF-9030, Silicone content 20%, from Shin-Etsu Chemical Co., Ltd.) | 1.0 |
| (5) (d) Dimethiconol gum (XF49-C2070, silicone content 20% from Momentive Performance Materials Inc.) | 1.0 |
| (6) (e) Triethylhexanoin | 1.0 |
| (7) Pantenol | 0.1 |
| (8) Ion-exchanged water | 0.05 |
| (9) Perfume | Appropriate amount |

Example 5

Hair Oil

The following ingredients (1)-(12) were stirred, dissolved and mixed to obtain a liquid hair oil.

| Ingredient | wt % |
|---|---|
| (1) (a) Isodecane | Balance |
| (2) (b) Dimethicone PEG block polymer (FZ-2250 from Dow Corning Toray Company Ltd.) | 5.0 |
| (3) (c) Ethanol | 10.0 |
| (4) (d) High molecular weight polysiloxane (KF-9030, Silicone content 20%, from Shin-Etsu Chemical Co., Ltd.) | 5.0 |
| (5) (d) Highly polymerized dimethiconol (XF49-C2497, silicone content 35% from Momentive Performance Materials Inc.) | 10.0 |
| (6) (e) Olive oil | 5.0 |
| (7) Squalane | 5.0 |
| (8) Dimethylpolysiloxane (20 cs) | 10.0 |
| (9) Soy lecithin | 1.0 |
| (10) Isostearoyl (wheat/corn/soy) amino acid AMP | 0.5 |
| (11) Tocopherol acetate | 0.1 |
| (12) Perfume | Appropriate amount |

Example 6

Hair Oil

The following ingredients (1)-(13) were stirred, dissolved and mixed to obtain a liquid hair oil.

| Ingredient | wt % |
|---|---|
| (1) (a) Isohexadecane | Balance |
| (2) (a) Decamethylcyclopentasiloxane | 20.0 |
| (3) (b) Dimethicone PEG block polymer (FZ-2233 from Dow Corning Toray Company Ltd.) | 5.0 |
| (4) (c) Ethanol | 15.0 |
| (5) (d) High molecular weight polysiloxane (KF-9028, silicone content 20%, from Shin-Etsu Chemical Co., Ltd.) | 10.0 |
| (6) (e) Tea seed oil | 1.0 |
| (7) Dimethylpolysiloxane (20 cs) | 10.0 |
| (8) Cross-linked methylpolysiloxane (KSG-15 from Shin-Etsu Chemical Co., Ltd.) | 5.0 |
| (9) Ethylhexyl methoxycinnamate | 1.0 |
| (10) t-butylmethoxydibenzoylmethane | 0.1 |
| (11) Bis ethylhexyloxyphenol methoxyphenyl triazine | 0.1 |
| (12) Di-(phytosteryl/octyldodecyl) lauroyl glutamate | 0.5 |
| (13) Perfume | Appropriate amount |

Example 7

Hair Oil

The following ingredients (1)-(11) were stirred, dissolved and mixed to obtain a liquid hair oil.

| Ingredient | wt % |
|---|---|
| (1) (a) Isodecane | Balance |
| (2) (a) Dimethylpolysiloxane (1.5 cs) (KF-96L-1.5 cs from Shin-Etsu Chemical Co., Ltd.) | 5.0 |
| (3) (b) Dimethicone PEG block polymer (FZ-2233 from Dow Corning Toray Company Ltd.) | 5.0 |
| (4) (c) Ethanol | 15.0 |
| (5) (d) High molecular weight polysiloxane (KF-9030, Silicone content 20%, from Shin-Etsu Chemical Co., Ltd.) | 5.0 |
| (6) (d) Amino-modified high molecular weight silicone 10% dimethylpolysiloxane solution (APS-10-DMS from Shin-Etsu Chemical Co., Ltd.) | 5.0 |
| (7) (e) *Camellia* seed oil | 10.0 |
| (8) Ethylhexyl methoxycinnamate | 1.0 |
| (9) Oxybenzone-3 | 0.1 |
| (10) Royal jelly extract | 0.5 |
| (11) Perfume | Appropriate amount |

INDUSTRIAL APPLICABILITY

The present invention provides a hair cosmetic mainly used as a hair oil that exhibits a superior sensation during use and superior stability over time.

The invention claimed is:

1. A hair cosmetic composition, said hair cosmetic composition comprising:
   (a) a 40-95 wt % volatile oil component;
   (b) a 0.1-20 wt % component of highly polymerized straight chain block-type polyoxyethylene/polyoxypropylene/butylene/dimethylpolysiloxane copolymer; and
   (c) 0.1-30 wt % ethanol, wherein said hair cosmetic composition is substantially free of water, and said component (b) has a formula of

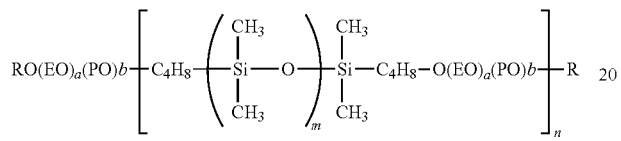

in which "R" represents an alkyl group, "a" represents an integer from 5 to 50, "b" represents an integer from 0 to 50, "m" represents an integer from 5 to 300, and "n" represents an integer from 1 to 40, wherein wt % refers to the mass percentage of the total amount of the composition.

2. The hair cosmetic composition of claim 1, further comprising:
   (d) at least one silicone rubber component having a polymerization degree of 3,000-20,000 selected from the group consisting of high molecular weight polysiloxane polymers, highly polymerized dimethicononol polymers, amino-modified high molecular weight silicone polymers, and ammonium-modified high molecular weight silicone polymers.

3. The hair cosmetic composition of claim 2, further comprising:
   (e) a component selected from a group consisting of plant oil, polar oil, and a mixture thereof, wherein said component (e) has at least one ester bond.

* * * * *